(12) United States Patent
Felix et al.

(10) Patent No.: US 6,613,941 B1
(45) Date of Patent: Sep. 2, 2003

(54) METHOD FOR RECOVERING FLUORINATED ALKANOIC ACIDS FROM WASTE WATERS

(75) Inventors: Bernd Felix, Burgkirchen (DE); Reinhard Sulzbach, Burghausen (DE); Stephan Führer, Burgkirchen (DE); Thomas Kaiser, Kelkheim (DE); Hagen Kniep, Frankfurt am Main (DE); Armin Budesheim, Wiesbaden-Naurod (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/700,636

(22) PCT Filed: May 27, 1999

(86) PCT No.: PCT/EP99/03672
§ 371 (c)(1),
(2), (4) Date: Nov. 16, 2000

(87) PCT Pub. No.: WO99/62858
PCT Pub. Date: Dec. 9, 1999

(30) Foreign Application Priority Data

Jun. 2, 1998 (DE) .......................................... 198 24 614

(51) Int. Cl.$^7$ .......................... C07C 53/21; C07C 51/43; C08L 3/00

(52) U.S. Cl. ...................... 562/605; 562/608; 554/177; 523/332; 252/302

(58) Field of Search ......................... 252/302; 554/177; 562/605, 608; 523/332

(56) References Cited

U.S. PATENT DOCUMENTS

| | | | |
|---|---|---|---|
| 3,882,153 A | 5/1975 | Seki et al. | 260/408 |
| 4,282,162 A | 8/1981 | Kuhls | 260/408 |
| 4,369,266 A | 1/1983 | Kuhls et al. | 523/332 |
| 5,017,480 A | 5/1991 | Mori et al. | 435/106 |
| 5,312,935 A | 5/1994 | Mayer et al. | 554/182 |
| 5,442,097 A | 8/1995 | Obermeier et al. | 560/227 |

FOREIGN PATENT DOCUMENTS

| | | | |
|---|---|---|---|
| DE | A 20 44 986 | 9/1970 | |
| EP | A 014 431 | 1/1980 | ............ B01J/49/00 |

Primary Examiner—Samuel Barts
Assistant Examiner—Sikarl A. Witherspoon
(74) Attorney, Agent, or Firm—James V. Lilly; Brian E. Szymanski

(57) ABSTRACT

Fluorinated emulsifier acids can be isolated from wastewater by firstly removing fine solids and/or material which can be converted into fine solids from the wastewater, preferably by precipitation, subsequently bringing the wastewater into contact with an anion-exchange resin and eluting the adsorbed emulsifier acids from the latter.

16 Claims, No Drawings

METHOD FOR RECOVERING FLUORINATED ALKANOIC ACIDS FROM WASTE WATERS

This application is a 371 of PCT/EP99/03672, filed May 27, 1999, published as WO 99/62858, on Dec. 9, 1999.

In the polymerization of fluorinated monomers in aqueous dispersion, use is made of fluorinated alkanoic acids as emulsifiers since they have no telogenic properties. In particular, use is made of the salts, preferably the alkali metal or ammonium salts, of perfluorinated or partially fluorinated alkanecarboxylic acids or alkanesulfonic acids. These compounds are prepared by electrofluorination or by telomerization of fluorinated monomers, which is costly. There have therefore been many attempts to recover these valuable materials from wastewater.

U.S. Pat. No. 5,442,097 discloses a process for the recovery of fluorinated carboxylic acids in usable form from contaminated starting materials. In this process, the fluorinated carboxylic acid is, if necessary, liberated from these materials in an aqueous medium using a sufficiently strong acid, the fluorinated carboxylic acid is reacted with a suitable alcohol and the ester formed is distilled off. The starting material can here be a polymerization liquor, in particular from an emulsion polymerization in which the fluoropolymer is prepared in the form of colloidal particles with the aid of relatively high amounts of emulsifier. This process has proven very useful, but requires a certain concentration of fluorinated carboxylic acid in the starting material.

From U.S. Pat. No. 4,369,266 it is known to pass a permeate from the ultrafiltration of fluoropolymer dispersions, containing fluorinated and stabilizing emulsifiers, over basic exchange resins in which the fluorinated emulsifier is retained and is recovered by subsequent elution.

DE-A-20 44 986 discloses a process for the recovery of perfluorocarboxylic acids from dilute solution, in which the dilute solution of the perfluorocarboxylic acids is brought into adsorption contact with a weak base anion-exchange resin and the perfluorocarboxylic acid present in the solution is thereby adsorbed on the anion-exchange resin, the anion-exchange resin is eluted with an aqueous ammonia solution and the adsorbed perfluorocarboxylic acid is thus transferred into the eluant and the acid is finally isolated from the eluate. However, complete elution requires relatively large amounts of dilute ammonia solution and this process is also very time-consuming. These disadvantages are overcome by the process known from U.S. Pat. No. 4,282,162 for the elution of fluorinated emulsifier acids adsorbed on basic anion exchangers, in which the elution of the adsorbed fluorinated emulsifier acid from the anion exchanger is carried out using a mixture of dilute mineral acid and an organic solvent. In this process, the ion-exchange resin is regenerated at the same time by use of the acid.

It has been found that this last-named process presents problems in industrial practice when, in particular, the wastewater processed contains very fine solids which in the past were often not recognized or at least not recognized as causing a problem. In this case, the apparatuses containing the anion-exchange resin become clogged with these solids more or less quickly, which becomes noticeable as a result of increased flow resistance and reduced performance. The upstream filters or frits customarily used are ineffective here.

It has also been found that these difficulties are caused by the fine solids being kept in relatively stable colloidal suspension by the emulsifier acids. When these acids are then removed from the system by means of the anion-exchange resin, this relatively stable dispersion is destroyed and the solid is precipitated and clogs the ion-exchange resin. It was thus also found that the performance of the process known from U.S. Pat. No. 4,282,162 can be considerably improved and also made suitable for wastewater containing fine solids if these solids are removed from the wastewater before it is brought into contact with the anion-exchange resin.

A further aspect of the invention is that it is possible to remove not only existing solids but also other interfering constituents which can be converted into solids. Such interfering constituents can be other acids or their salts which are likewise bound to the ion-exchange resin and thus not only tie up ion exchange capacity but may also require special precautions during and/or after elution of the emulsifier acids.

An example of such an interfering acid is oxalic acid which is frequently used as a buffer. The addition of calcium ions in stoichiometric amounts or in an excess or deficiency, for example as chloride or hydroxide, enables all or some of the oxalic acid to be precipitated as sparingly soluble oxalate, advantageously together with any further interfering, finely divided solids present.

The invention accordingly provides a process for the recovery of fluorinated emulsifier acids from wastewater, which comprises firstly removing fine solids and/or material which can be converted into fine solids from the wastewater, subsequently binding the fluorinated emulsifier acids on an anion-exchange resin and eluting the fluorinated emulsifier acids from the latter. Further aspects of the invention and their preferred embodiments are described in more detail below.

Wastewater suitable for treatment is waste process water in which surface-active fluorinated alkanoic acids are present. The process is particularly suitable for wastewater from the polymerization of fluorinated monomers by the emulsion method, in which the fluorinated monomer is converted in the presence of a relatively high concentration of fluorinated emulsifier acid and with mild stirring into a finely divided polymer which is in finely dispersed, colloidal form and in which the latex obtained is coagulated, for example by intensive stirring, after the desired solids concentration has been reached, so that the polymer precipitates as a fine powder.

It has been found that in the known work-up it is especially relatively low molecular weight polymer material which causes difficulties; the adverse effect of these low molecular weight polymers becomes particularly noticeable when the polymerization process leads to a broad molecular weight distribution. In the case of such "difficult" wastewater too, the process of the invention displays its capabilities.

The method of removing the fine solids depends on the particular circumstances:

In the case of acidic wastewater, it can be sufficient to carry out a—possibly partial—neutralization with suitable bases such as calcium hydroxide, resulting in precipitation of the colloid—and any precipitatable substances such as oxalate ions present—while the emulsifier acid or its salt remain in solution.

Another possible way of precipitating the interfering colloids is the addition of suitable metal salts, for example aluminum salts such as aluminum chloride and aluminum sulfate, calcium salts such as calcium chloride, magnesium salts such as magnesium chloride and magnesium sulfate, iron salts such as iron(II) chloride or iron(III) chloride and iron sulfate. In the case of acidic wastewater, the addition of corresponding metals such as aluminum, iron or magnesium is also possible. To improve the flocculation, small amounts of a flocculant can also be added.

A further possible way of precipitating the interfering colloids is electrocoagulation. Here, an electric field is applied to the wastewater to coagulate the colloidal particles. In the case of inert electrodes (for example titanium), the particles deposit on the surfaces. In the case of soluble electrodes (for example iron and/or aluminum), metal cations having a high charge: diameter ratio are introduced into the solution and these effect coagulation as in the case of addition of metal salts. An advantage of electrocoagulation is that it avoids the additional introduction of anions such as chloride or sulfate. To improve flocculation, small amounts of a flocculant can be added.

Suitable mechanical methods of removing the fine solids are crossflow filtration (for example using membranes, centrifuges), deep bed filtration (for example sand bed filters) or precoat filtration with addition of a filter aid (for example cellulose, perlite, kieselguhr).

The precipitated solids can be separated off in a manner known per se, for example by filtration, if necessary using a filter aid, by decantation, by flotation or sedimentation.

The adsorption of the emulsifier acids onto ion-exchange resins can be carried out in a manner known per se. Suitable resins are, in particular, strong base anion-exchange resins as are obtainable, for example, under the trade names ®AMBERLITE IRA-402, ®AMBERJET 4200 (both Rohm & Haas), ®PUROLITE A845 (Purolite GmbH) or ®LEWATIT MP-500 (Bayer AG).

The adsorption can be carried out in a manner known per se, with the ion-exchange resins being located in customary apparatuses such as tubes or columns through which the wastewater flows.

The elution of the bound emulsifier acids is likewise carried out in a manner known per se, with preference being given to the method described in U.S. Pat. No. 4,282,162.

Methods suitable for isolating the emulsifier acids in the high purity required for use in polymerization are, for example, those described in the abovementioned U.S. Pat. No. 5,442,097 or that described in U.S. Pat. No. 5,312,935 in which the eluate is firstly substantially freed of water and then treated with oxidizing agents.

The wastewater remaining after adsorption of the emulsifier acids is treated in a known manner, depending on the content of other materials or returned to the process. If desired, residual fluorinated emulsifier acids can be removed using customary adsorbents such as activated carbon.

The invention is illustrated by the following examples.

EXAMPLE 1

The starting material used is wastewater from the copolymerization of tetrafluoroethylene (TFE) and perfluoro(n-propyl vinyl ether) (PPVE), in which the ammonium salt of n- and iso-perfluorooctanoic acid (PFOA) in a molar ratio of 9:1 is used as emulsifier. The PFOA concentration in the liquor is 1200 mg/l and the oxalic acid concentration is 1600 mg/l.

In a stirred vessel, 14 l of the liquor are admixed with 1.5 g/l of a 10% strength by weight aluminum chloride solution and stirred vigorously. The precipitate which forms is filtered off.

About 50 ml of a commercial strong base ion-exchange resin (®AMBERLITE IRA-402, Rohm & Haas; styrene-divinylbenzene type, anion: chloride, gel, total capacity: 1.3 eq/l, bulk density: 710 g/l) are introduced into a cylindrical glass column (length: 25 cm, diameter: 16 mm) provided with a glass frit and rinsed with water. To load the ion exchanger, the pretreated liquor is pumped upward through the column at a linear velocity of 1 m/h by means of a pump, the water leaving the column is collected and the PFOA concentration is determined for the mass balance. After loading, the column is rinsed with 100 ml of water.

To regenerate the ion exchanger, 150 ml of a mixture of 89% by weight of methanol, 7% by weight of concentrated sulfuric acid and 4% by weight of water are passed through the column at a linear velocity of 0.5 m/h and the eluate is collected. The column is subsequently rinsed with 100 ml of water.

The eluate contains 85% of the emulsifier acid present in the wastewater and 3900 mg/l of oxalic acid.

EXAMPLE 2

In a stirred vessel, 14 l of the liquor as in Example 1 are admixed with 1.5 g/l of a 10% strength by weight aluminum chloride solution and stirred vigorously. The pH is subsequently adjusted to 7.5 using 10% strength by weight milk of lime. The precipitate which forms is filtered off and the pH of the solution is adjusted to 4 using dilute sulfuric acid.

Set-up and procedure for loading and regeneration of the ion exchanger are analogous to Example 1.

Here, the eluate contains 95% of the emulsifier acid present in the wastewater and 1 mg/l of oxalic acid.

EXAMPLE 3

16 l of wastewater from the work-up of fluorinated polymers are placed in a stirred vessel. The polymerization uses the ammonium salt of PFOA as emulsifier, and the PFOA concentration is 1200 mg/l. 2 g of a 10% strength by weight aluminum chloride solution are added to this solution and the mixture is stirred vigorously. 10% strength by weight milk of lime is subsequently added to bring the pH to 7.5 and 3 mg/l of a flocculant (®PRAESTOL A 3015 L, Stockhausen GmbH & Co. KG; polyacrylamide) are added. The precipitate which forms is filtered off and the pH is adjusted to 4 using sulfuric acid.

Loading and regeneration of the ion exchanger are carried out as in Example 1.

Here, the eluate contains 91% of the emulsifier acid present in the wastewater.

COMPARATIVE EXAMPLE

The starting material used is a mother liquor from the copolymerization of TFE and PPVE, in which the ammonium salt of PFOA is used as emulsifier. The PFOA concentration is 1200 mg/l.

About 50 ml of the strong base ion-exchange resin specified in Example 1 are introduced into a cylindrical glass column (length: 25 cm, diameter: 16 mm) provided with a glass frit and rinsed with water. To load the ion exchanger, the untreated liquor is pumped upward through the bed by means of a pump. The pressure drop over the ion exchanger bed is measured using a manometer. The loading experiment had to be stopped after 400 ml of the liquor had been passed through, since the resin became conglutinated as a result of precipitated polymer.

What is claimed is:

1. A process for the recovery of fluorinated emulsifier acids from wastewater, which comprises firstly removing interfering constituents which are selected from fine solids and material which can be converted into fine solids from the wastewater, and subsequently binding the fluorinated emulsifier acids on an anion-exchange resin and eluting the fluorinated emulsifier acids from the latter.

2. The process as claimed in claim 1, wherein the fine solids are precipitated.

3. The process as claimed in claim 1 or 2, wherein the interfering constituents are removed by precipitation.

4. The process as claimed in claim 1 or 2, wherein the interfering constituents are mechanically removed.

5. The process as claimed in one of claims 1, 2 and 4, wherein the interfering constituents are separated off by sedimentation.

6. The process as claimed in one of claims 1, 2 and 4, wherein the interfering constituents are separated off by flotation.

7. A process for the recovery of fluorinated emulsifier acids from wastewater which comprises providing wastewater from the polymerization of fluorinated monomers comprising fine solids and/or material which can be converted into fine solids and oxalic acid, treating the wastewater with an aluminum salt solution while mixing intensively, subsequently adjusting the pH to a value in the range from 6 to 7.5 by means of milk of lime, filtering off the precipitate which forms and, after adjusting the pH of the solution to a value below 7 using sulfuric acid, and passing the solution over an ion exchanger.

8. The process of claim 7, wherein the anion-exchange resin used is a strong base anion-exchange resin.

9. The process of claim 7, wherein elution of the fluorinated emulsifier acid from the anion-exchange resin is carried out using a mixture of dilute mineral acid and an organic solvent.

10. The process of claim 1, wherein the anion-exchange resin used is a strong base anion-exchange resin.

11. The process of claim 1, wherein elution of the fluorinated emulsifier acid from the anion-exchange resin is carried out using a mixture of dilute mineral acid and an organic solvent.

12. A process for the recovery of fluorinated emulsifier acids from wastewater, which comprises providing wastewater from the polymerization of fluorinated monomers comprising interfering constituents selected from the group consisting of fine solids and material which can be converted into fine solids, removing the interfering constituents from the wastewater, and subsequently binding the fluorinated emulsifier acids on an anion-exchange resin.

13. The process of claim 12, wherein the interfering constituents are removed via a process selected from mechanical removal, sedimentation, and flotation.

14. The process of claim 12, further comprising eluting the fluorinated emulsifier acids from the anion-exchange resin.

15. The process of claim 14, wherein the anion-exchange resin used is a strong base anion-exchange resin.

16. The process of claim 14, wherein elution of the fluorinated emulsifier acid from the anion-exchange resin is carried out using a mixture of dilute mineral acid and an organic solvent.

* * * * *

UNITED STATES PATENT AND TRADEMARK OFFICE
CERTIFICATE OF CORRECTION

PATENT NO. : 6,613,941 B1  
DATED : September 2, 2003  
INVENTOR(S) : Felix, Bernd It is certified that error appears in the above-identified patent and that said Letters Patent is hereby corrected as shown below:

<u>Title page, Item [54] and Column 1, lines 1-3,</u>
"METHOD FOR RECOVERING FLUORINATED ALKANOIC ACIDS FROM WASTE WATERS" should be shown as -- PROCESS FOR THE RECOVERY OF FLUORINATED ALKANOIC ACIDS FROM WASTEWATER --

Signed and Sealed this

Ninth Day of March, 2004

JON W. DUDAS  
*Acting Director of the United States Patent and Trademark Office*